US010232139B1

United States Patent
Hang et al.

(10) Patent No.: US 10,232,139 B1
(45) Date of Patent: Mar. 19, 2019

(54) SMART PILLOW COVER AND ALARM TO IMPROVE SLEEPING AND WAKING

(71) Applicant: CHRONA SLEEP, INC., Mesa, AZ (US)

(72) Inventors: Zimin Hang, St. Louis, MO (US); Blake Sakran, Smithton, IL (US); Alan Sze, Lexington, MA (US); Shaun Vaidyan, St. Louis, MO (US)

(73) Assignee: CHRONA SLEEP, INC., Mesa, AZ (US)

( * ) Notice: Subject to any disclaimer, the term of this patent is extended or adjusted under 35 U.S.C. 154(b) by 207 days.

(21) Appl. No.: 15/181,222

(22) Filed: Jun. 13, 2016

Related U.S. Application Data

(60) Provisional application No. 62/174,683, filed on Jun. 12, 2015.

(51) Int. Cl.
    *A61M 21/00* (2006.01)
    *A61M 21/02* (2006.01)
    *A61B 5/00* (2006.01)

(52) U.S. Cl.
    CPC .......... *A61M 21/02* (2013.01); *A61B 5/4812* (2013.01); *A61M 21/00* (2013.01); *A61M 2021/0016* (2013.01); *A61M 2021/0022* (2013.01); *A61M 2021/0027* (2013.01); *A61M 2021/0044* (2013.01); *A61M 2021/0083* (2013.01); *A61M 2205/50* (2013.01); *A61M 2230/63* (2013.01)

(58) Field of Classification Search
    CPC ..... A61M 21/05; A61M 21/00; A61B 5/4812; A61B 5/4806
    USPC .................................................. 600/26–28
    See application file for complete search history.

(56) References Cited

U.S. PATENT DOCUMENTS

| 3,884,218 A | 5/1975 | Monroe |
| 4,335,710 A | 6/1982 | Williamson |
| 4,736,751 A | 4/1988 | Gevins et al. |
| 4,834,701 A | 5/1989 | Masaki |
| 5,036,858 A | 8/1991 | Carter et al. |
| 5,213,562 A | 5/1993 | Monroe |

(Continued)

FOREIGN PATENT DOCUMENTS

| EP | 1886707 | 2/2008 |
| WO | WO/2005028029 | 3/2005 |

(Continued)

OTHER PUBLICATIONS

Ngo, et al. Auditory closed-loop stimulation of the sleep slow oscillation enchances memory, Neuron 78, May 8, 2013, pp. 545-553.*

(Continued)

*Primary Examiner* — John P Lacyk
(74) *Attorney, Agent, or Firm* — Knobbe, Martens, Olson & Bear LLP

(57) ABSTRACT

A pillow cover device for promoting for a user restorative sleep and minimizing sleep inertia and fatigue upon waking comprising at least one non-invasive brain stimulator for stimulation of the brain at various selected frequencies; an alarm; sensors to monitor sleep; and a microprocessor, wherein the sensors provide the microprocessor data regarding the state of sleep of the user; wherein the microprocessor calculates brain activity indicating deep sleep slow-wave activity and activates the at least one brain stimulator to emit low frequency tones.

6 Claims, 15 Drawing Sheets

(56) References Cited

U.S. PATENT DOCUMENTS

| | | | |
|---|---|---|---|
| 5,409,445 | A | 3/1995 | Rubins |
| 6,468,234 | B1 | 10/2002 | Van der Loos |
| 7,041,049 | B1 | 5/2006 | Raniere |
| 7,166,070 | B2 | 1/2007 | Lawlis et al. |
| 7,749,154 | B2 | 7/2010 | Cornel |
| 7,868,757 | B2 | 1/2011 | Radivojevic et al. |
| 8,029,431 | B2 | 10/2011 | Tononi |
| 8,096,960 | B2 | 1/2012 | Loree, IV et al. |
| 8,267,851 | B1 | 9/2012 | Kroll |
| 8,276,851 | B2 | 9/2012 | Kroll |
| 8,382,424 | B1 | 2/2013 | Liang |
| 8,437,843 | B1 | 5/2013 | Kayyali et al. |
| 8,628,462 | B2 | 1/2014 | Berke et al. |
| 8,755,879 | B2 | 6/2014 | Hang et al. |
| 8,766,879 | B2 | 6/2014 | Fujikawa et al. |
| 8,870,764 | B2 | 10/2014 | Rubin |
| 2002/0007124 | A1 | 1/2002 | Woodward |
| 2005/0107722 | A1 | 5/2005 | Ozaki et al. |
| 2006/0152378 | A1 | 7/2006 | Lokhorst et al. |
| 2006/0293608 | A1 | 12/2006 | Rothman et al. |
| 2006/0294608 | A1 | 12/2006 | Hilton et al. |
| 2008/0081941 | A1 | 3/2008 | Tononi |
| 2008/0191885 | A1 | 8/2008 | Loree, IV et al. |
| 2008/0304691 | A1 | 12/2008 | Lai |
| 2011/0112442 | A1 | 5/2011 | Meger et al. |
| 2011/0178377 | A1 | 7/2011 | Heneghan et al. |
| 2011/0295083 | A1* | 12/2011 | Doelling ............... A61B 5/103 600/301 |
| 2012/0029322 | A1 | 2/2012 | Wartena et al. |
| 2012/0142999 | A1 | 6/2012 | Albu et al. |
| 2012/0265054 | A1 | 10/2012 | Olson |
| 2013/0023740 | A1 | 1/2013 | Kirchner et al. |
| 2013/0035541 | A1 | 2/2013 | Kashima et al. |
| 2015/0141879 | A1 | 5/2015 | Harper et al. |
| 2015/0230750 | A1 | 8/2015 | McDarby et al. |
| 2015/0258301 | A1 | 9/2015 | Trivedi et al. |
| 2017/0043118 | A1 | 2/2017 | Karp et al. |
| 2017/0087330 | A1 | 3/2017 | Kahn et al. |
| 2017/0258398 | A1 | 9/2017 | Jackson |
| 2018/0078197 | A1 | 3/2018 | Ware et al. |
| 2018/0078198 | A1 | 3/2018 | Reich et al. |
| 2018/0078732 | A1 | 3/2018 | Keshavan et al. |
| 2018/0078733 | A1 | 3/2018 | Freed et al. |
| 2018/0110960 | A1 | 4/2018 | Youngblood et al. |
| 2018/0132635 | A1 | 5/2018 | Loos |

FOREIGN PATENT DOCUMENTS

| | | |
|---|---|---|
| WO | WO/2012153263 | 11/2012 |
| WO | WO/2014/118654 | 7/2014 |

OTHER PUBLICATIONS

Ngo, et al. Induction of slow oscillations by rhythmic acoustic stimulation, J. Sleep Res. (2013) 22, pp. 22-31.

Ngo, et al. Auditory closed-loop stimulation of the sleep slow oscillation enhances memory, Neuron 78, May 8, 2013, pp. 545-553.

Bellesi, et al. Enhancement of sleep slow waves: underlying mechanisms and practical consequences, Frontiers in Systems Neuroscience, vol. 8 : Article 8,Oct. 2014, pp. 1-17.

Guerrero-Mora et al., "Sleep-wake Detection Based on Respiratory Signal Acquired Through a Pressure Bed Sensor," 34th Annual International Conference of the IEEE EMBS, San Diego, CA, Aug. 28-Sep. 1, 2012.

Nilsson, et al., "Foot-mounted inertial navigation made easy," 2014 International Conference on Indoor Positioning and Indoor Navigation Oct. 2014.

* cited by examiner

SMART PILLOW COVER AND ALARM TO IMPROVE SLEEPING AND WAKING

CROSS-REFERENCE TO RELATED APPLICATIONS

This application claims the benefit of provisional patent application No. 62/174,683 filed on Jun. 12, 2015, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to determining sleep states, and more particularly to determining deep sleep, enhancing deep sleep for restoration and memory consolidation, and transitioning from deep sleep to light sleep before waking to avoid sleep inertia.

In recent times, sleep has become a research topic of great interest. Sleep is a universal animal behavior that has significant import in modern human development and productivity. As a result, there is great motivation to study sleep, its benefits and the benefits that may be derived from optimizing sleep on an individual basis.

Electroencephalography (EEG) has been used pervasively in sleep research as a data collection tool due to its advantages in the field. It collects reliable data non-invasively by measuring electric signals at the scalp. During sleep, EEG signals have properties and behaviors that are largely invariant among varied populations. From EEG data, researchers have been able to accurately typify sleep stage cycles from EEG signals.

Sleep is known to be an episodic process with various stages, starting from a light state of sleep to a deep state of sleep and back to the light state. When awoken during a light state of sleep, post-waking fatigue and sleep inertia (e.g. the desire to return to a sleeping state while waking) are reduced in physiologically healthy patients. Sleep stages can be typified by brainwave patterns and brainwaves during light sleep are similar to brainwaves while awake. The theta waves (4-7 Hz) that occupy most of Stage 1 and 2 sleep are significantly more analogous to the alpha waves (high frequency, i.e., 8-12 Hz) that dominate our awake state than the delta waves (low frequency, i.e., 0.5-2 Hz) of deep sleep.

Most neural state changes (ex. being asleep to being awake) require some period of time for neurochemical and metabolic elements to direct the change; going from a state of light sleep to an awake state is faster than going from a state of deep sleep to an awake state. Because the transition from light sleep to an awake state is rapid, the duration of sleep inertia and fatigue should be minimized, as light state brainwave patterns are the most analogous to those observed in the awake state.

Currently, people are sleeping far less than the suggested optimal amount of an average of 8.4 hours per night due to a variety of factors, such as increased work hours, second or third jobs, longer commutes, increased media options, such as satellite television or internet websites, and family commitments. If people were getting enough sleep in their daily lives there would be little use for alarm clocks, as we would awaken naturally once the body had received enough sleep. However, since people are cutting into their optimal levels of sleep, alarm clocks are necessary to prematurely awaken sleepers.

For curtailed sleep, one of the most critical factors in determining the duration of Sleep Inertia is the sleep stage immediately preceding awakening. Abrupt awakening during deep sleep (e.g., Slow Wave Sleep or stage 3 or 4 sleep) produces greater Sleep Inertia than awakening during REM sleep or during light sleep (e.g., stage 1 or 2 sleep). In addition, sleep debt caused by prior sleep deprivation prolongs the effects of Sleep Inertia.

Another issue concerns the time course of Sleep Inertia. In a fully rested person awakened during deep sleep, duration of Sleep Inertia may rarely exceed 30 minutes. However, because the average working person is carrying a large sleep debt, realistically, the duration of Sleep Inertia may exceed 3.5 hours, depending on the sleep state immediately preceding awakening. A more conservative middle ground estimates the duration of Sleep Inertia to be between one and two hours.

Another sleep issue is the need to enhance various qualities of sleep, including deep NREM stage sleep. Disclosed in U.S. Pat. No. 5,213,562 is one method of inducing states of consciousness through generation of stereo audio signals having specific wave shapes which act as a carrier of a binaural beat. The resultant binaural beat acts to entrain brain waves into unique waveforms characteristic of identified states of consciousness. This method is applicable in areas of learning and behavior replication as well as in the area of sleep inducement techniques.

The binaural beat phenomenon was discovered in 1839 by H. W. Dove, a German experimenter. Generally, this phenomenon works as follows. When an individual receives signals of two different frequencies, one signal to each ear, the individual's brain detects a phase difference or differences between these signals. When these signals are naturally occurring, the detected phased difference provides directional information to the higher centers of the brain. However, if these signals are provided through speakers or stereo earphones, the phase difference is detected as an anomaly. The resulting imposition of a consistent phase difference between the incoming signals causes the binaural beat in an amplitude. The use of this technique requires the use of two earphones, each of which is transmitting a different frequency. FIG. 7 is an illustration of a scan of the results this technique.

Another method of inducing or promoting slow-wave activity (SWA) in the brain of a resting person thought to be associated with the restorative aspects of sleep by using an external repeated stimulus that promotes slow-wave activity. Slow wave activity, as used herein, includes slow waves and related phenomenon such as "sleep spindles". It is believed the invention may promote restful sleep for those who have trouble sleeping and/or shorten the amount of sleep needed by others. The stimulus may be applied at a time when the brain is susceptible to slow-wave sleep and may be turned off at any time, allowing the person to wake up on demand without grogginess beyond naturally occurring sleep "inertia". This method uses periodic stimulation of brain at a frequency substantially less than five Hz to promote slow wave activity. The brain stimulator may in one embodiment be audio signals such as short tones.

The present invention uses a pillow topper design that integrates unobtrusive mechanical sensors with a wide applicability of stimulation for all sensory modalities. Unlike prior art devices, the present invention does not use a wearable or obtrusive implementation for capturing and processing physiological data to gauge a user's sleep depth. The present invention uses a pillow topper design that integrates unobtrusive mechanical sensors with a wide applicability of stimulation for all sensory modalities.

Additionally, because of the lack of earphones or other attachment device, the present invention uses novel means of stimulation that enhance the quality of sleep.

Related Art

Prior art devices have been used for enhancing sleep. U.S. Pat. No. 8,029,431 discloses a device that uses low frequencies to stimulate slow-wave (deep sleep) activity. However, this device, and none of the devices disclosed below use high frequencies (8-12 Hz) to induce a change of state from deep sleep to light sleep preceding the scheduled alarm wake-up time.

Examples of known prior art devices are described in the references listed below, which are hereby incorporated by reference. U.S. Pat. No. 8,029,431B2 uses transcranial magnetic stimulation to induce sleep. The device can use electrodes, magnetic coils, earbuds, eye-masks, or headphones. US20080304691A1 uses a headband that covers the ears to emit sounds. Neither of the above references disclose the claimed invention.

SUMMARY OF THE INVENTION

A pillow top device for promoting for a user restorative sleep and minimizing sleep inertia and fatigue upon waking comprising at least one non-invasive brain stimulator for stimulation of the brain at various selected frequencies; an alarm; sensors to monitor sleep; and a controller, wherein the sensors provide the controller data regarding the state of sleep of the user; wherein the controller calculates brain activity indicating deep sleep slow-wave activity and activates the at least one brain stimulator to emit low frequency tones; wherein at a pre-determined transition time, the controller activates the brain stimulator to emit high frequency tones to transition the user to light sleep; and wherein at the pre-determined alarm time, the controller activates the alarm to awaken the user.

In another embodiment, the invention is a pillow top or pillow cover device comprising at least one non-invasive brain stimulator for stimulation of the brain at various selected frequencies; at least one sensor to monitor sleep; and a controller, wherein the at least one sensor provides the controller data regarding the state of sleep of the user; wherein the controller calculates brain activity indicating deep sleep slow-wave activity and activates the at least one brain stimulator to emit low frequency tones; wherein the tone emissions are monaural tones that are dynamic and are selected from the group consisting of timbre, pitch, rhythm, and volume.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
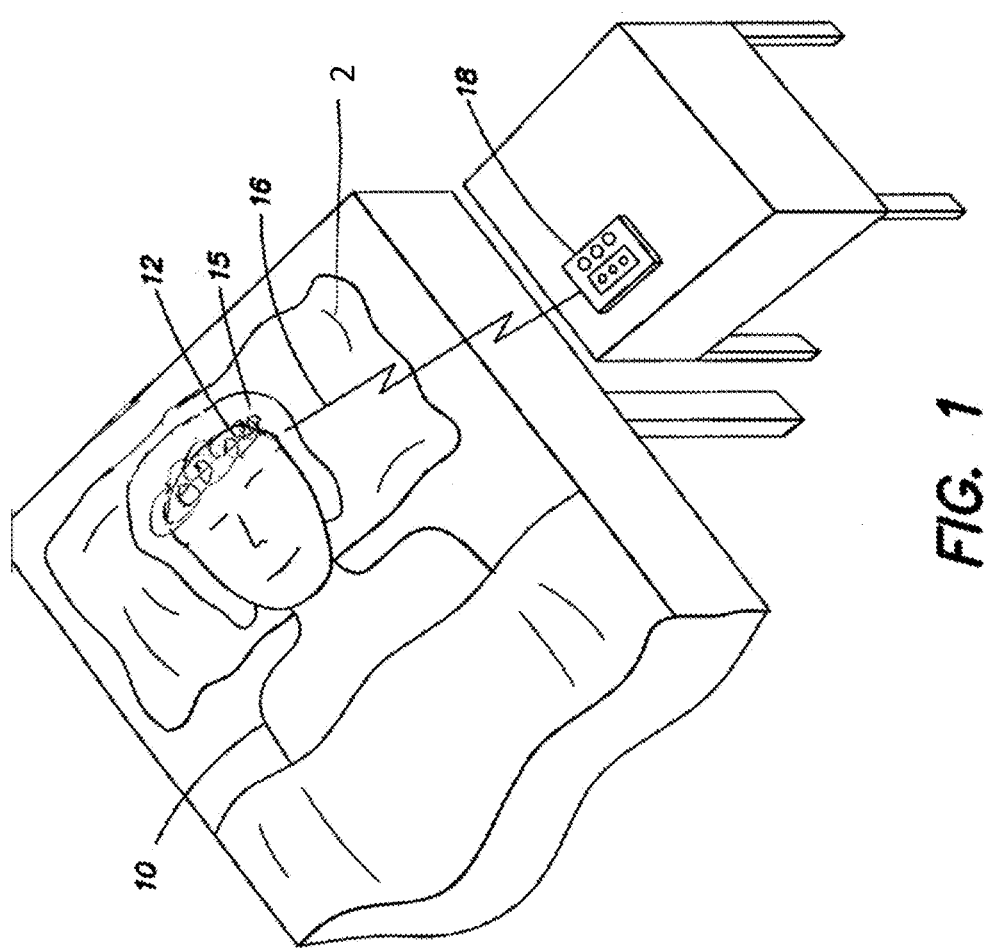
FIG. 1 is a perspective view of a user using an embodiment of the device of the present invention.
Figure 2:
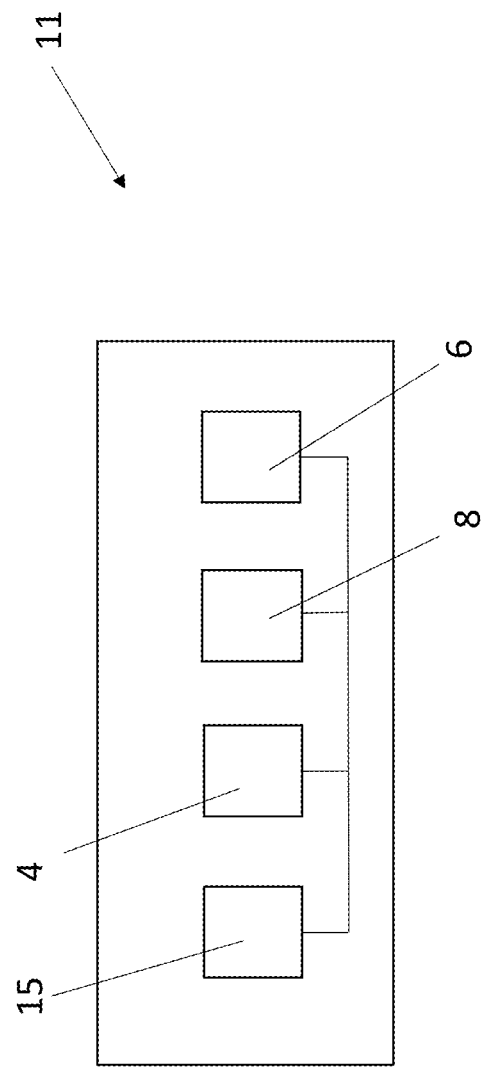
FIG. 2 is a schematic block diagram of an embodiment of the device.

FIGS. 1 and 2 show an illustrative embodiment of a wake-up device in accordance with the invention. In this embodiment, the wake-up device includes a pillow top 2 containing a monitoring portion 11. Separately, there is an alarm portion 18. In a preferred embodiment, the alarm is in the pillow topper as well and includes at least one speaker 4 and a vibrator 6. Monitoring portion 11 may include one or more sensors, such as accelerometer 8, for monitoring a biosignal of the user 10, and a device 15 including electronic circuitry and/or other components to predict an occurrence when the user 10 may be in a desired sleep state. In a preferred embodiment the accelerometer 8 is a MPU6050 IMU sensor. Although the monitoring portion 11 need not necessarily contact the user 10, in this embodiment the monitoring portion is in the pillow topper on which the user's head rests. Other sensor arrangements may be used, whether contacting or non-contacting, to detect one or more biosignals of the user, such as body temperature, temperature gradients, blood pressure, galvanic skin response, eye or other body movement, etc. However, any number of sensors may be used in any location as the present invention is not intended to be limited in this respect.

The device 15 may process information from the sensors 8 using any suitable algorithm, for example, to determine the sleep state of the user. In addition, the device 15 may predict when the user will be in a deep sleep state, for example using the algorithm shown in FIG. 6. After receiving from the sensor signals that the user is in deep sleep, the device 15 may send an output to the speakers 4 to emit low frequency tones (less than 5 Hz) to enhance deep sleep. At the set transition time, the device 15 may send an output to the speakers to emit high frequency tones (from 8 to 12 Hz) to transition the user from deep sleep to light sleep. At a predetermined wake-up time, the device 15 sounds an alarm to wake the user 10. The monitoring portion 11 and the alarm portion 18 may communicate in any suitable way, such as by wired or wireless link 16 (which may include any suitable communication network(s)). Based on information from the monitoring portion 11, the alarm portion 18 may awaken the user 10 using any means, such as a buzzer, a radio, a flashing light, and/or any other suitable means.

Figure 3:
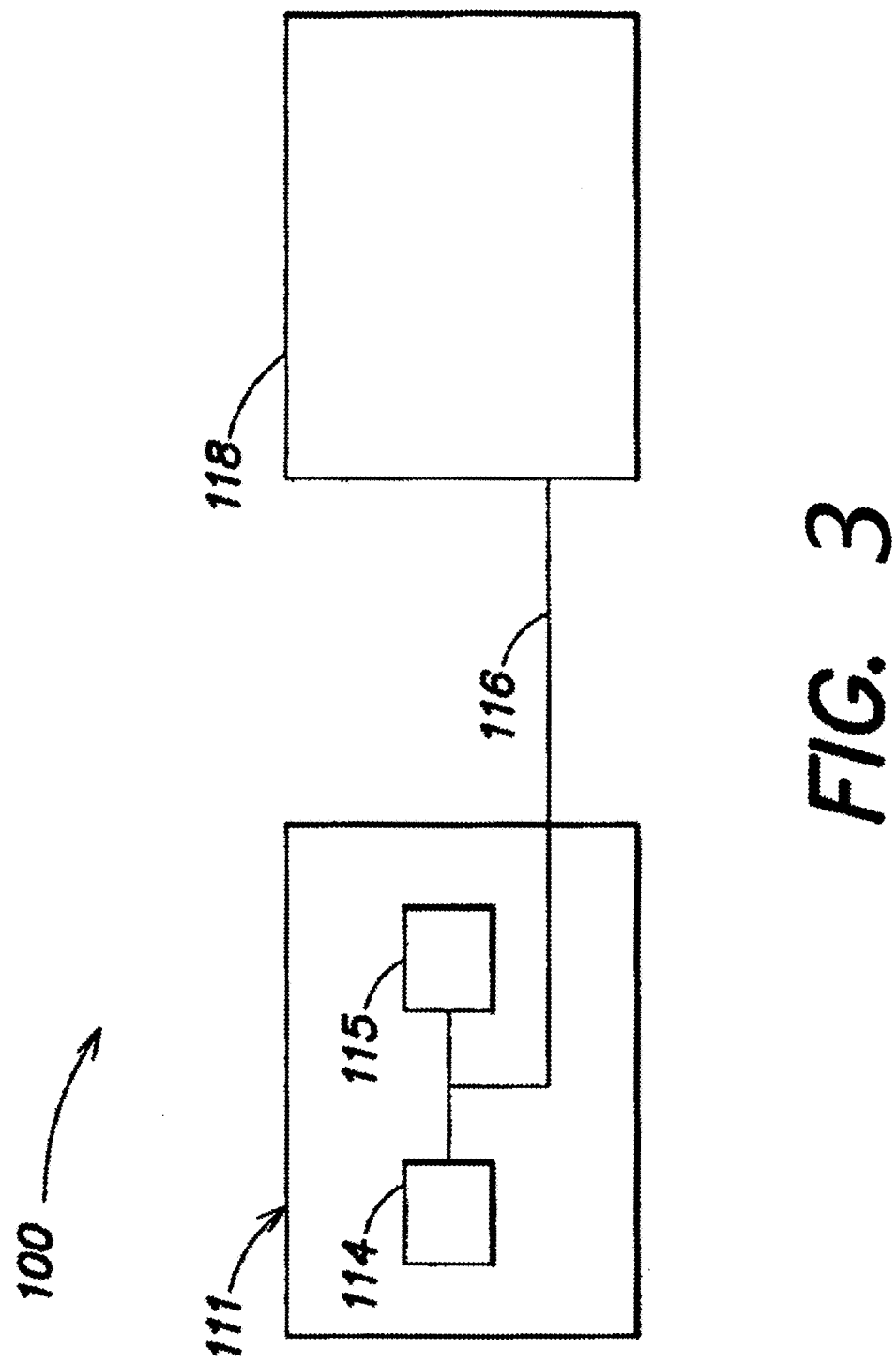
FIG. 3 is a schematic block diagram of an embodiment of the device.

As shown in FIG. 3, in a preferred embodiment, the monitoring portion 111 include a predicting portion 115 that may assist in determining the sleep state of the user and may use sensed information from the sensing portion 114, a sleep history of a user from prior sleep periods, a pre-determined hypnogram, any combination thereof or any other device or information as long as predicting portion 115 may determine in what state of sleep the user currently is. Thus, the predicting portion 115 may use any suitable data or algorithms, such as the wake-up algorithm described in the embodiment in FIG. 6. The sleep state of the user is actively monitored and this information is used in actively readjusting any predicted occurrences.

In addition to sleep state information from sensing portion 114, a wake-up condition may be indicated to the predicting portion 115. Since the user will likely enter the desired sleep state more than once throughout the night, to guide the wake-up device in predicting during which occurrence of the desired sleep state the user wishes to be awakened, a wake-up condition is induced by the use of a high frequency tone to move the user from deep sleep to light sleep. In one embodiment, the user may set a wake-up time at which the user wishes to be awakened. In that event, at a predetermined time interval preceding the wake up time, the high frequency tones are emitted.

Alarm portion 118 may also perform additional functions and contain additional accoutrements. A speaker may be used to project sound to awaken the user from sleep. An AM/FM radio, cassette, CD or MP3 player and the appropriate controls may be included with alarm portion 118 for projection via the speaker. Alarm portion 118 may also contain a light which may be activated at desired times, as determined by monitoring portion 111, to expose the user to light. Light exposure may inhibit melatonin production; therefore, a user may be more likely to awaken gracefully after being exposed to light. In a preferred embodiment, the alarm 118 is located in the pillow topper and uses speakers and a vibrator. The volume emitted by the speakers may be adjusted by the position of the user's head, wherein the closer to the speaker, the lower the volume of noise emitted, and the farther away, the louder the volume of noise.

Figure 4:
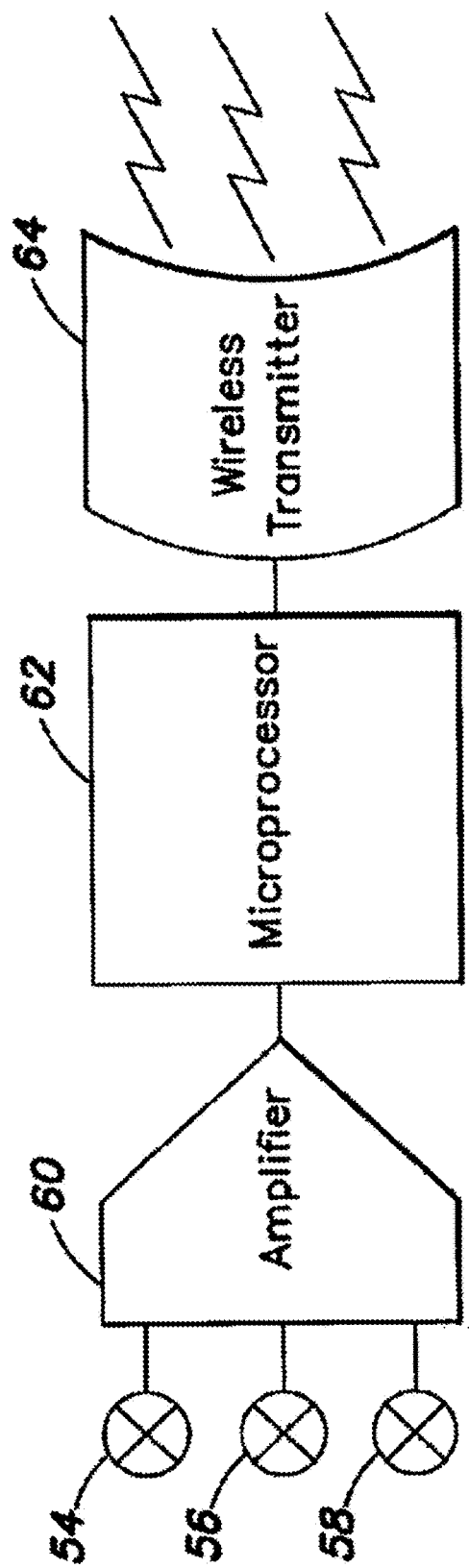
FIG. 4 is a schematic block diagram of the sensor part of the device.

As shown in the embodiment depicted in FIG. 4, the pillow topper may include three sensors 54, 56, 58. Signals from these sensors 54, 56, 58 may connect to a circuit board (not shown) and may be amplified by amplifier 60. Amplifier 60 may use a large gain to bring the differential between signal sensors 54, 56 up to a level where it can be used as an input into an Analog to Digital Converter (ADC), which, in some embodiments, may be integrated into a microprocessor 62. The amplified signals may be converted to a digital signal by the ADC, which may use a Right Leg Driver (DRL) system to eliminate common mode noise.

Figure 5:
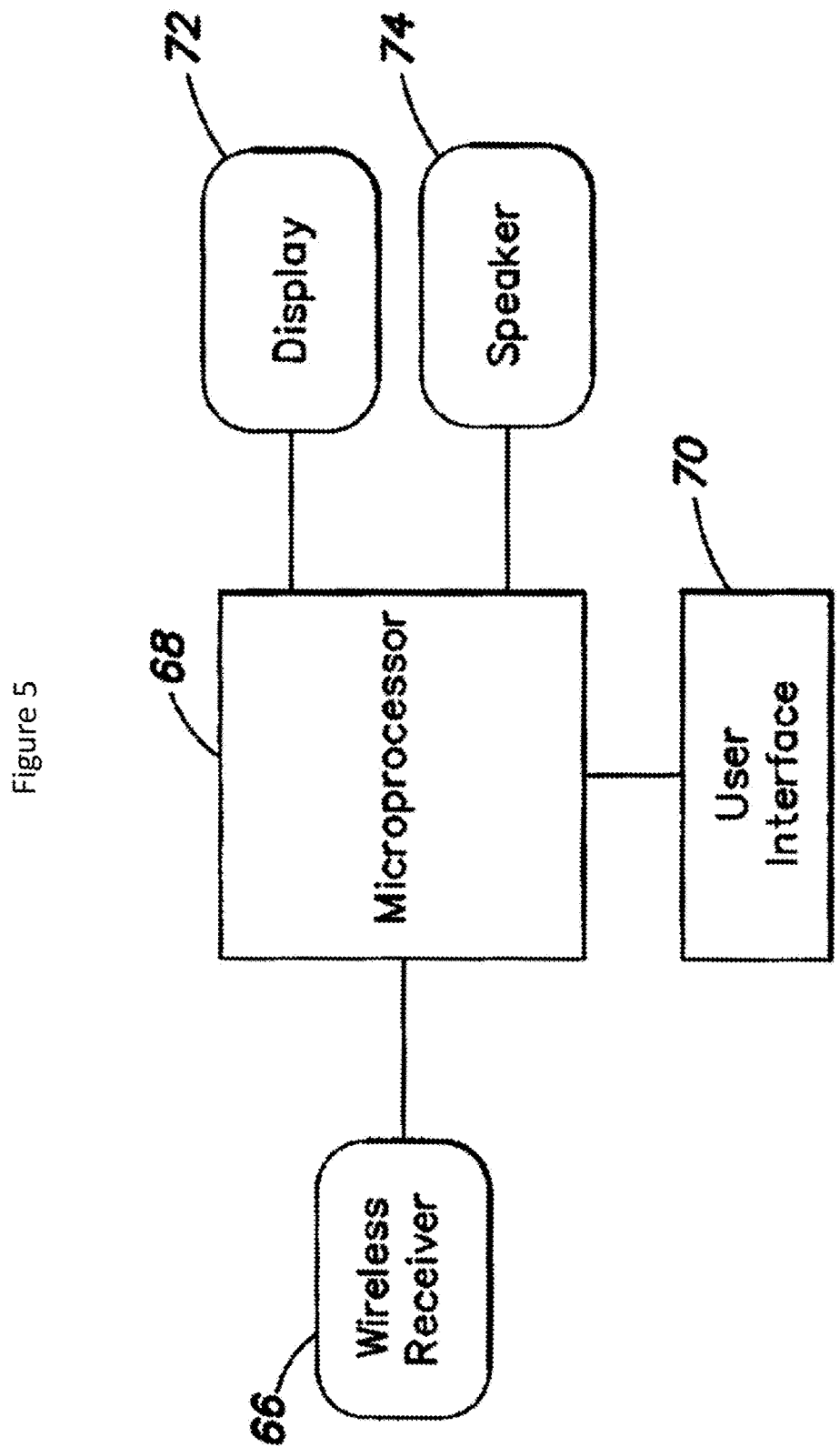
FIG. 5 is a schematic block diagram of the clock part of the device.

The digital signal may be read by microprocessor 62 at defined signal transit times. The microprocessor 62 may determine the transmit times based on predetermined values and may wirelessly transmit the digital signal to the alarm clock unit, an embodiment of which is shown in FIG. 5, using the wireless transmitter 64. Microprocessor 62 may arrange wireless transmission times to minimize power usage. In addition, the wireless transmitter may be, but need not be, integrated onto microprocessor 62. Alternatively, in some embodiments, wireless transmission may not be necessary.

As shown in the embodiment shown in FIG. 5, the alarm unit may include a wireless receiver 66 to communicate with the pillow topper unit, for example, using electromagnetic waves for transmission. A Digital Signal Processor (DSP) 68 on the alarm may analyze the received data from the pillow topper according to the sleep state detection algorithm. The DSP 68 may also run the wake-up algorithm, and decide when to awaken the user.

In one embodiment, the user may choose a napping mode, wherein the user may be awakened at the end of an optimal nap time, such as 20 minutes. The optimal nap time may be set so that the user may avoid entering deep sleep; however, other times may be used. In addition, the user may set a wake-up time, so that the user may not have to worry about not being awakened by an appropriate time. For example, if a user has a 4 p.m. appointment and lies down for a nap at 3 p.m., but does not actually fall asleep until 3:30 p.m. the user may set a wake-up time of 3:55 p.m. so that the user will not oversleep.

Figure 10:
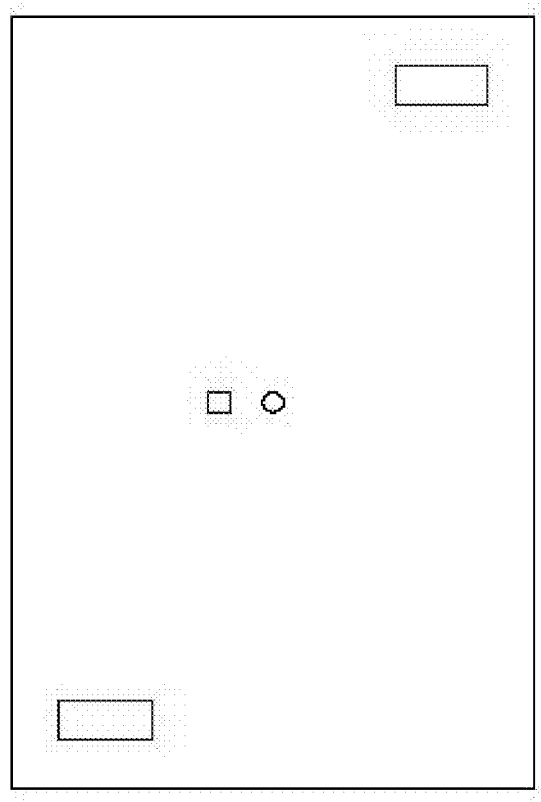
FIG. 10 is an embodiment of the present invention pillow topper device.
Figure 11:
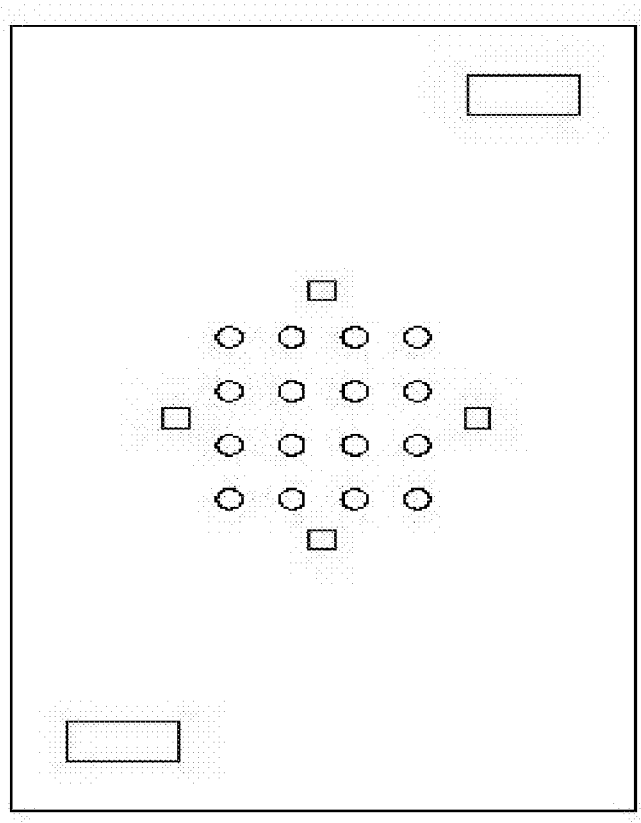
FIG. 11 is an embodiment of the present invention pillow topper device.

In another embodiment, as shown in FIGS. 10 and 11, the pillow top device 22 may include the mechanical sensors 28 used singularly or as an array of accelerometers, ranging from one to sixteen. The array of accelerometers capture motion data indicative of movement. The data is further processed to determine whether the captured motion is physiological (hypnic jerk), environmental (pets jumping bed), and the origin of the motion is (e.g. head twitch vs leg jerk) to predict sleep depth and to determine the type of neurostimulation administered. The devices of FIGS. 10 and 11 further show at least one speaker 24 and at least one vibrator 26.

The use of mechanical sensors to capture physiological data in a pillow topper form is low-fidelity but adequate for use of predicting sleep depth or determining the delivery of neurostimulation. For purposes of illustration and not limitation, a number of features can be extracted from the motion captured from one accelerometer that are indicative of sleep depth, such as magnitude or standard deviation. These features can be processed using algorithms that use machine to classify the user's state of sleep.

An increased number of mechanical sensors in an array can capture finer movements and be used to extract additional features such as heart rate and respiratory, where the force displacements require more sensitive motion capturing.

In this embodiment, the stimulation used by the device are further optimized for the pillow topper form to determine the best intensity or location of stimulation. For instance, if the user is lying on her side, acoustical stimulation in one speaker may be louder than the other, compared to if she's lying on her back, where the speakers would then have a balanced acoustical output.

In another embodiment, the mechanical sensors are used to determine the pillow type that the user has installed the device onto. A calibration step where the user puts her head down onto the device and pillow will enable the mechanical sensors to capture motion data that differs based on the type of the pillow. For instance, a softer down pillow is compressed at a constant, faster rate than a memory foam pillow, which is compressed more rapidly at first and then at a slower rate following initial distribution of force.

The present invention uses mechanical sensors for capturing physiological data related to sleep through a pillow topper implementation in order to maximize comfort. Although the mechanical sensors are unable to capture data indicative of sleep depth at as high fidelity as optical methods (i.e. for capturing heart rate) or electrophysiological methods (i.e. for capturing brainwave activity), it can be used to determine sleep depth with sufficient accuracy for non-invasive stimulation to be effectively applied.

Figure 12:
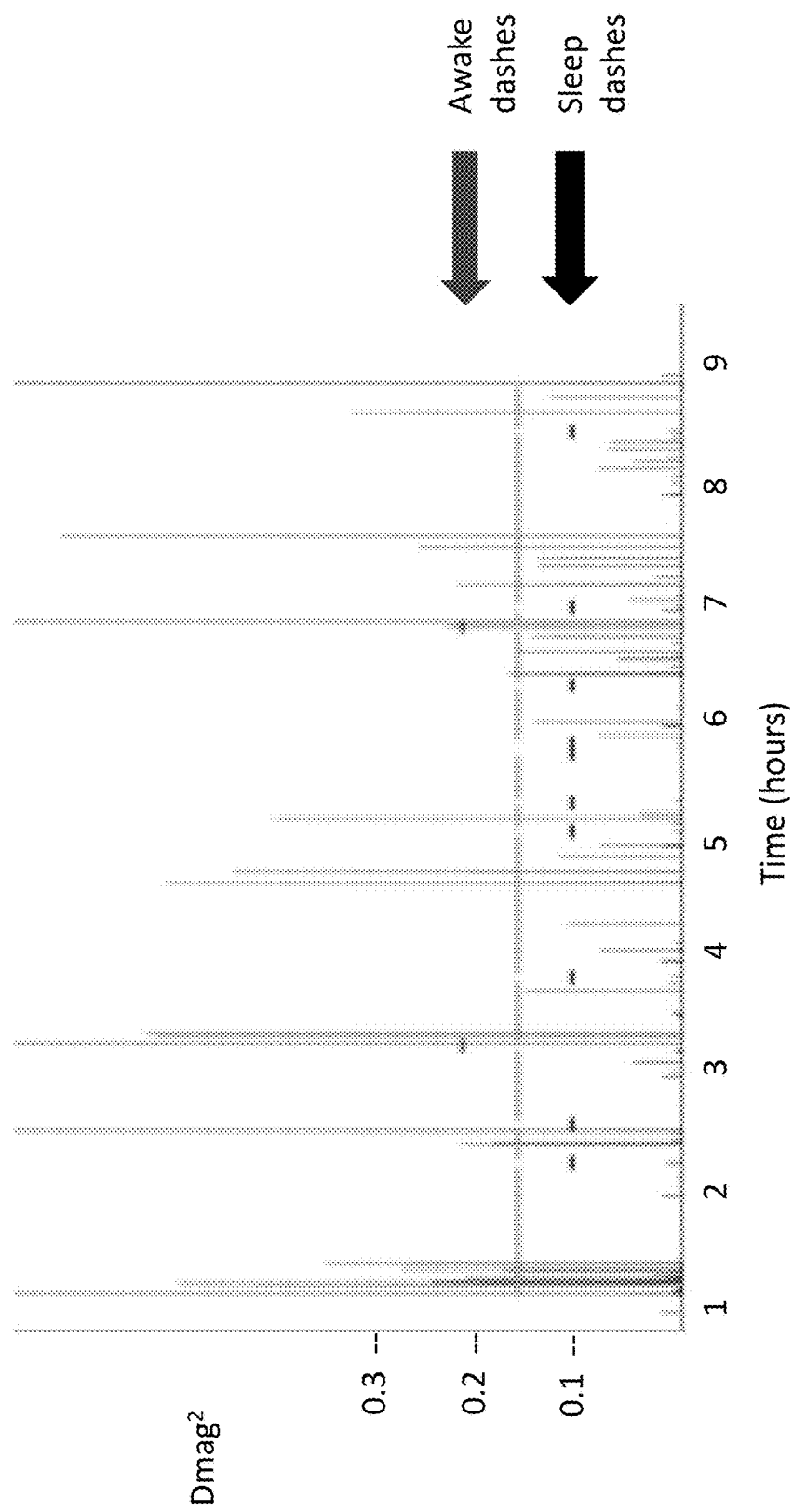
FIG. 12 is a scan of motion data captured through the mechanical sensors of the present invention pillow topper device.

The present invention, through accelerometer readings of head and torso motion, is able to predict whether the user is awake, in light sleep, or in deep sleep, as shown in the time scan of FIG. 12. In FIG. 12, motion data is captured using the motion sensors shown in FIGS. 10 and 11 and analyzed. The data is processed to determine periods of deep sleep, shown graphically in the sleep dashes, and periods of wakefulness, shown graphically in the awake dashes.

When the device determines the user is in deep sleep, the non-invasive sleep inducing stimulation is applied, and there is an enhancement in sleep quality as shown in brain electrophysiology. The use of mechanical sensors in a pillow topper implementation is shown to be sufficient for predicting sleep depth and application of non-invasive stimuli.

In one embodiment, gyroscopes are used to capture motion data indicative of movement. This data is further processed and used to predict sleep depth or determine the delivery of neuro stimulation.

In one embodiment, thin force sensors are used to capture motion data indicative of movement. This data is further processed and used to predict sleep depth or determine the delivery of neuro stimulation.

In one embodiment, pressure sensors are used to capture motion data indicative of movement. This data is further processed and used to predict sleep depth or determine the delivery of neuro stimulation.

An increased number of mechanical sensors in an array can capture finer movements and be used to extract additional features such as heart rate and respiratory, where the force displacements require more sensitive motion capturing.

In one embodiment, the mechanical sensors are additionally used to determine position and orientation of the user on top of the pillow topper. The array(s) of mechanical sensors can be distributed throughout the pillow to capture the dispersion of movements throughout the pillow topper to determine the positioning and orientation of how the user is interfacing the pillow topper.

Figure 8:
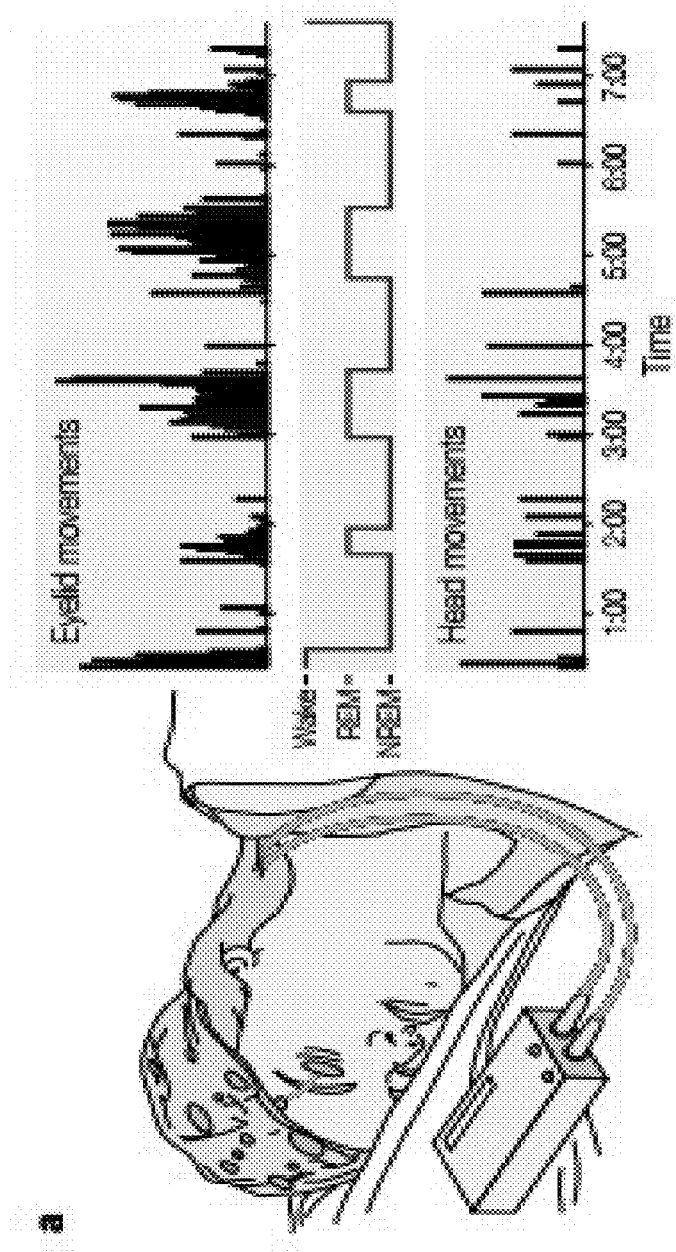
FIG. 8 is a prior art invention using a cap to capture head movements.
Figure 9:
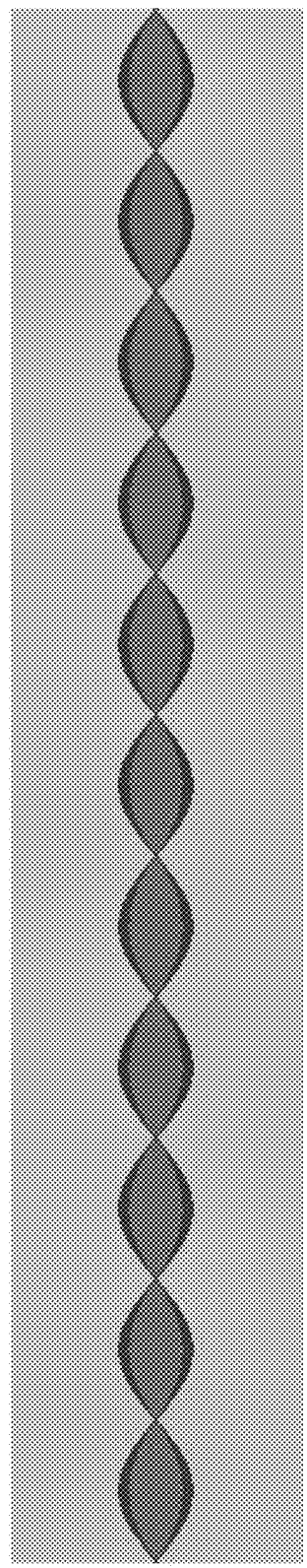
FIG. 9 is a time-amplitude plot of monoaural acoustic waveform.

Mechanical sensors in the pillow topper are able to capture fine movements of the head, neck, and torso. Prior art devices using a cap, such as is shown in FIG. 8, capture such movements. However, in the present invention, such a cap is not necessary.

Research suggests that sleep is not a unitary phenomenon and that there are hemispheric differences in sleep. Thus, a method capturing motion from the head and torso, as does the present invention, may observe less bias with regard to lateral differences in bodily motions. Wrist-worn sensors, worn on either right or the left wrist, would be much more likely to have such bias.

In one embodiment of the invention, the pillow topper may have an array of 4 or more mechanical sensors that are processed to capture heart and respiratory rate through processing minute physical displacements caused by a heartbeat or inhale/exhale. A wrist worn device is limited by spatial capacity to be able to capture heart rate or respiration using mechanical sensors.

Using the data captured by the mechanical sensors, the present invention processes the data to predict sleep depth, and then delivers non-invasive stimulation. Unlike previous methods, the pillow topper implementation is not sensory modality-specific. For instance, eye-masks are optimized for delivery of photic stimulation by directly interfacing and contacting the eyes. Headphones are optimized for delivery of acoustic stimulation by directly interfacing and contacting the ears. The present invention is a broader method of delivering all types of non-invasive stimulation.

In one embodiment, the invention contains speakers in the pillow topper deliver acoustic stimulation to enhance deep sleep. It is known that stimulation at less than 1 Hz (notably 0.8 Hz) promote slow wave activity in the brain (Ngo et al., 2013). There are many mechanisms of using acoustic stimulation to enhance slow wave activity. For purposes of illustration and not limitation with respect to stimulation modality, acoustic stimulation methods for enhancing deep sleep are exemplified below to show the many ways of using the auditory modality.

Figure 7:
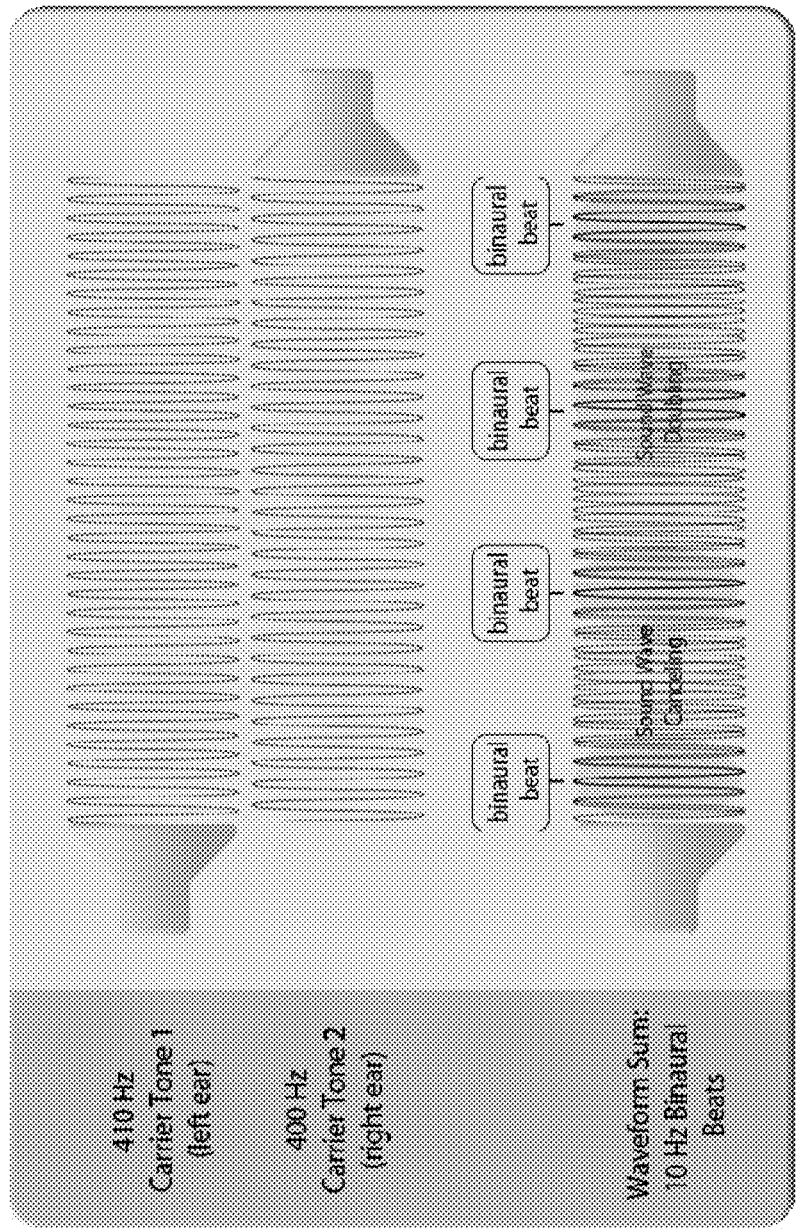
FIG. 7 is a prior art time-amplitude plot of binaural stimulation.

As is disclosed in the prior art, binaural stimulation, shown in FIG. 7, is used to entrain for slow wave rhythms via the superior olivary nucleus. Binaural simulation uses constant waveforms at different pitches to generate an efferent from the superior olivary nucleus. The superior olive functions to localize the source of sounds, and in this method it is manipulated to create a rhythmic oscillation at the third frequency that the brain interprets as novel. In normal conditions, the superior olivary nucleus only receives input from lower-level auditory pathways from the ears to determine the source of the sounds. Binaural stimulation using two different frequencies (e.g. 400 Hz and 410 Hz) to manipulate the superior olive to creates an efferent at a third frequency of 10 Hz that then entrains the brain. This manipulation of the superior olive is required to keep the stimulation effective with use by not habituating. However, this technique requires the use of headphone speakers. The present invention claims a pillow topper form that does not require any wearable or visible device to delivery acoustic stimulation for enhancing sleep.

Figure 6:
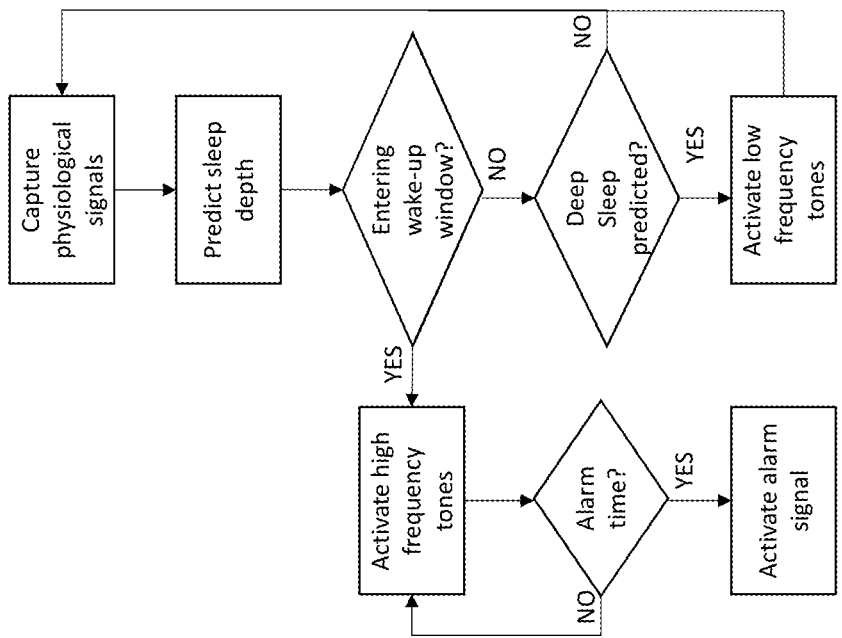
FIG. 6 is a schematic representation of a wake-up algorithm.

Monaural stimulation can be used without headphone speakers to entrain for slow wave rhythms. Static monaural stimulation is shown in FIG. 6 which is an example of a monaural acoustic waveform emitted by speakers in the device in a time-amplitude plot (horizontal-time, vertical-amplitude). However, when static monaural stimulation is used through the present invention, the activation along the auditory pathway does not create the third oscillatory frequency through the superior olivary nucleus, and the stimulus can become ineffective due to habituation. Known methods suggests that this direct/low-level use of the auditory pathways (i.e. no activation of the superior olivary nucleus) precludes the monaural stimulation method from being effective for extended periods of time due to the brain's ability to habituate to constant stimuli. Thus, the present invention uses dynamic stimuli to overcome the brain's habituation processes.

Figure 13:
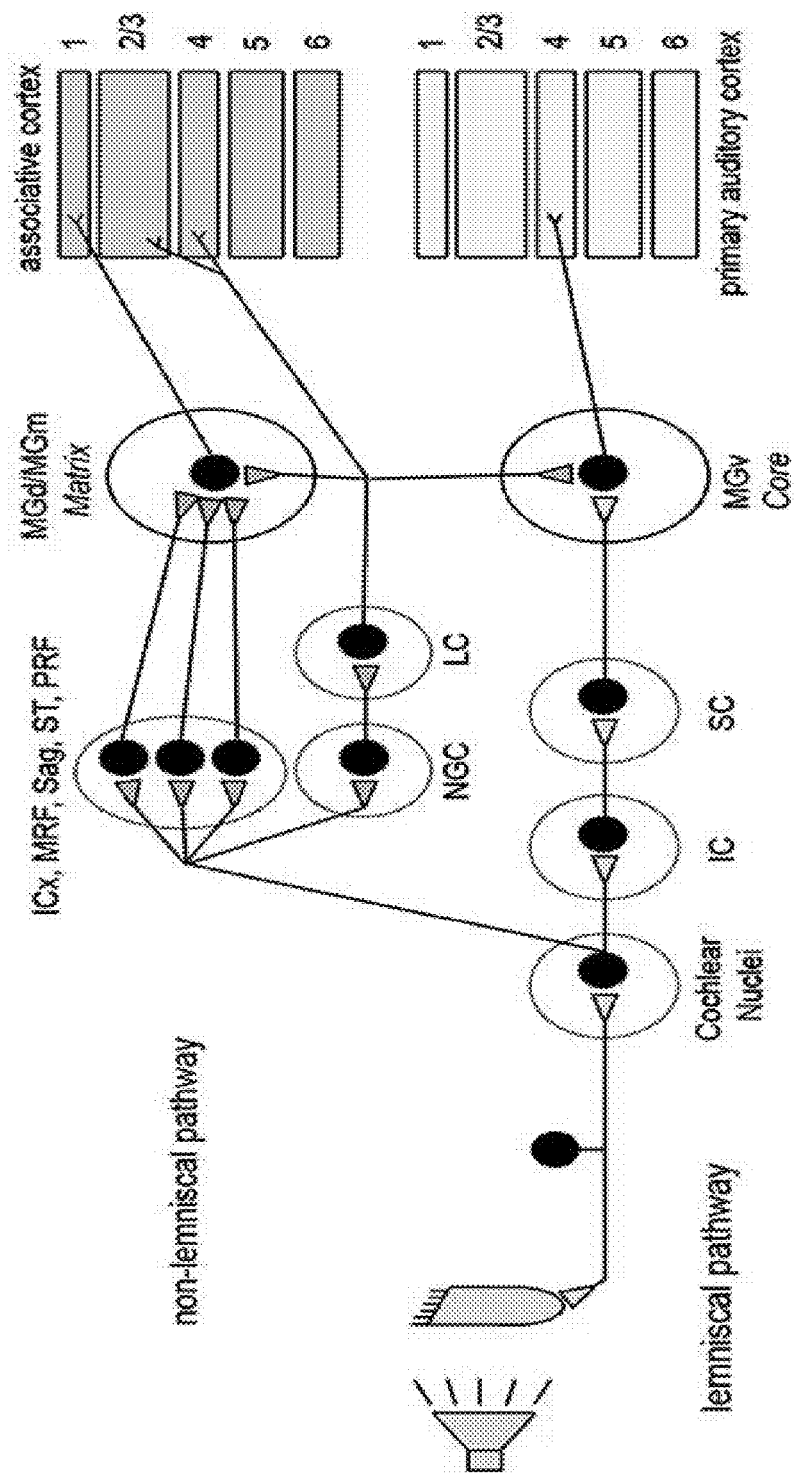
FIG. 13 is a diagram of the lemniscal pathway and the non-lemniscal pathway.

In (Bellesi et al., 2014), a non-lemniscal pathway is proposed for use by auditory stimulation to enhance slow wave sleep. As shown in FIG. 13 where the non-lemniscal pathway is outlined, the regions mediating this cortically projecting pathway (i.e. used for entrainment), notably the dorsal and caudo-medial MGB (MGd/MGm) and locus coeruleus (LC), show rapid habituation to repetitive stimuli. As such, binaural stimulation can be effective over time because the oscillatory nature of the third frequency created by the superior olivary nucleus preserves its novelty, and its effectiveness with use.

Figure 14:
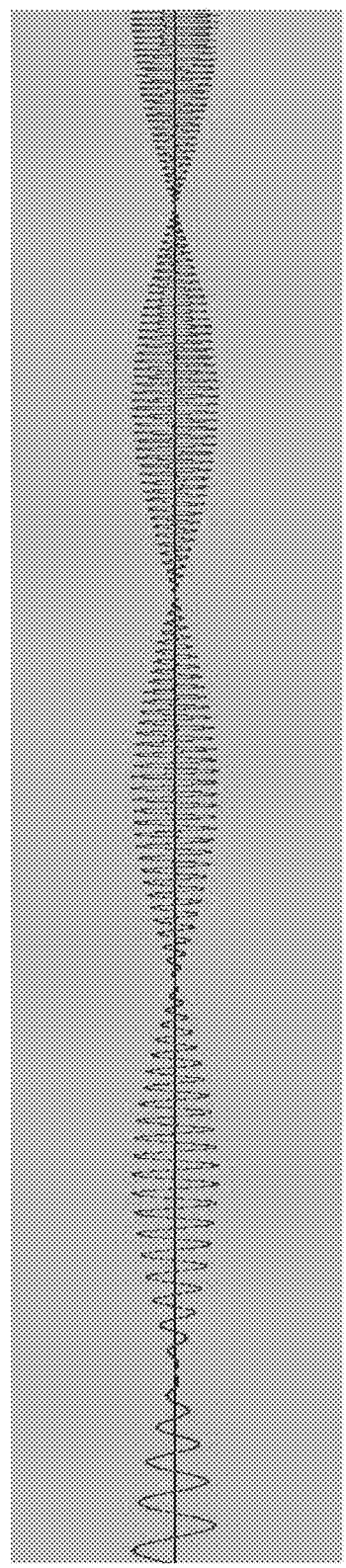
FIG. 14 is plot of dynamic pitch modulated monaural stimulation of the present invention.
Figure 15:
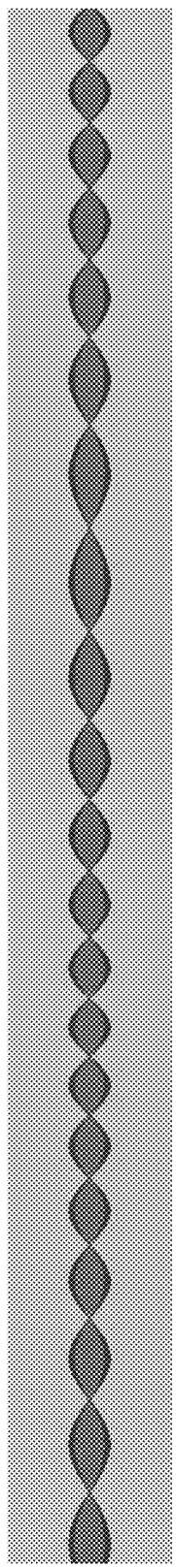
FIG. 15 is a plot of dynamic rhythm modulated monaural stimulation of the present invention.

The present embodiment of this invention, however, does not use binaural stimulation nor monaural stimulation. It uses dynamic (changing) monaural stimulation to prevent habituation (ineffectiveness with continued use) by constantly changing the composition of the sounds used for monaural stimulation. Such dynamic sound includes, but is not limited to the changing of timbre of the sound (e.g. from a pure tone to a cello-type sound and back), the pitch of the sound (e.g. varying from 250 Hz to 300 Hz over a 2-minute period) as shown in FIG. 14; the rhythm of the sound (e.g. oscillating from 0.75 Hz to 0.9 Hz over a 20-second period as shown in FIG. 15; or the volume of the sound (e.g. oscillating from 30 dB to 35 dB over a 2-minute period).

The dynamic changing of timbre of the sound from a pure tone to a cello-type sound and back can be done with a single timbre of multiple timbres. For example, the timbers could range from timber-1 to timber-2 to timber-3 to timber-4 to timber-5 at 10 second intervals, the cycle back to timber-1 at a 30 second interval. Further, length of the cycle can vary widely from 1 second to 10 minutes. In a preferred embodiment, the cycle can range from 10 seconds to 5 minutes. Further, one skilled in the art could program additional variances, where there are multiple timbers and multiple cycles, creating a dynamic sound.

The dynamic changing of the pitch of the sound can vary from 20 Hz to 20,000 Hz. over a period of from 1 second to 10 minutes. In a preferred embodiment, the pitch can vary from 250 Hz to 300 Hz over a 2-minute period. Further, one skilled in the art could program additional variances, where there are multiple pitches and multiple cycles (periods), creating a dynamic sound.

The dynamic changing of the rhythm of the sound can be oscillating frequencies from about 0.1 Hz to 10 Hz over a period of about 1 second to about 10 minutes. In a preferred embodiment, the sound frequency oscillates from about 0.75 Hz to 0.9 Hz over a 20-second period as shown in FIG. 15. Further, one skilled in the art could program additional variances, where there are multiple frequencies and multiple cycles (periods), creating a dynamic sound.

The dynamic changing of the volume of the sound can be made by oscillating from about 20 dB to 50 dB over a period of from about 10 seconds to 10 minutes. In a preferred embodiment, the volume oscillates from 30 dB to 35 dB over a 2-minute period. Further, one skilled in the art could program additional variances, where there are multiple volumes and multiple cycles (periods), creating a dynamic sound.

These elements are used distinctly or combined to adjust the level of novelty (PN) to fit the user for optimal enhancement of sleep. There are many possible factors that determine the best PN for each user, including but not limited to depth of sleep, time since sleep onset, sleep pressure (i.e. accumulated sleep debt), general stress (i.e. cortisol and cortisol precursors in the blood), hearing sensitivity (sensitivity toward other sensory modalities would be accounted for respective of the present invention's stimulation used).

By keeping the monaural stimuli dynamic, the present invention shows a novel method that overcomes the known limitation of monaural stimulation being unable to sustain effectiveness over time. The novel method allows monaural stimulation to be comparably effective as binaural stimulation, and also allows for non-wearable, unobtrusive implementations such as in a pillow topper, which is an improvement over the previously required headphones or earbuds.

Another limitation of non-wearable devices is that they're not entirely personal, which may cause significant variation in effectiveness. Sleeping on one's back versus on one's side changes the dynamic as the ears are in different locations, and in the case of side sleeping, one ear is covered entirely. The present invention has been tested and shown to be a novel method that is effective regardless of head orientation/placement (so long as the user does not fall off the pillow entirely), and regardless of variable auditory dynamics given changing relationships between speakers and the user's ears.

There are many forms of stimulation for every sensory modality, of which acoustic is the most well-known, that can be used for manipulating the brain's electrophysiology or physiological sleep state. For purposes of illustrating and not limiting, the present invention uses novel methods of acoustic stimulation that adapts the known inventions requiring wearables to enhance sleep using a pillow topper implementation that does not directly interface the ears. The present invention takes the most unobtrusive form within the pillow topper design in order to deliver stimulation at maximum comfort, through novel methods of stimulation that are alternatively effective and does not require any obtrusive elements such as wearables or TMS.

Another embodiment of the invention there are arrays of lights emitting diodes in the pillow topper to provide photic stimulation. The embodiment is not the optimal form for photic stimulation to enhance sleep because it does not interface and contact the eyes directly and consistently, however the present invention delivers photic stimulation with significant effectiveness through dynamic stimulation. For instance, the photic stimulation may change over time its composition of frequency of light (i.e. color) or amplitude (i.e. luminosity).

Another embodiment of the invention there are arrays of scent nodes in the pillow topper that release compounds contained in lavender oil, vetiver oil, vanillin, or other pleasant odors. The embodiment does not interface the nasal region directly, but can still deliver the stimulation for effective enhancement.

In another embodiment of the invention there are arrays of vibrating motors embedded in the pillow topper. These motors deliver haptic stimulation to enhance deep sleep but may also function to entrain other rhythms associated with REM or used to wake the user.

The use of non-invasive methods of stimulation via endogenous pathways can be used to enhance deep sleep by entraining or promoting slow wave activity. They can also be used to enhance REM sleep by use of higher energy stimulation, such as in the alpha- or beta-frequency band acoustical stimulation. They can also be used to induce lucid dreaming during REM by use of gamma-frequency band acoustical stimulation. In these methods of enhancing a state of sleep, the nature of the stimulation is rhythmic or constant. Another limitation of non-wearable devices being not entirely personal is that they may interfere with persons sleeping nearby, which problematic most notably for acoustic stimulation (as well as photic and olfactory stimulation). The present invention uses a threshold-level acoustic stimulation that has been tested to show to not interfere with persons who share a bad with the user when both persons are asleep. Although there are cases where the user is asleep while the person next to the user is awake, and the present invention activates and the awake person hears the device, the sound is marginal and does not cause disturbances for the awake person.

Rhythmic or constant stimulation, such as repetitive droning or a flat pink noise stimulation, promote synchronization in brainwave activity via the frequency-following response. To promote a state of wakefulness, intermittent stimulation in irregular intervals can serve to desynchronize brainwave activity. The present invention may use any combination of non-invasive methods of stimulation through the pillow topper to promote waking or various states of sleep by use of intermittent or rhythmic stimulation, respectively.

The present invention improves upon previous methods of using mechanical sensors for capturing physiologically significant motion through its positioning underneath the head, neck, and torso, and its spatial capacity for implementing arrays of sensors. Additionally, the present invention does not require any wearables and is invisible in its implementation (i.e. underneath the pillow case).

In one embodiment, an array of one accelerometer is at the center of the pillow topper along with a vibrating motor, and two speakers on opposite corners See FIG. 10. The placement of the speakers in this embodiment is optimal for delivery of acoustical stimulation in a balanced manner, while minimizing the possibility of overstimulation in the scenario where the user is sleeping on her side and her ears are directly over the speakers.

The accelerometer data is processed into magnitude data and extracted into features that are representative of different types and intensities of physiologically significant movements. In one embodiment the processing is done locally in the pillow topper. In another embodiment the processing is transmitted wirelessly to a portable device such as a mobile phone, where the processing occurs remotely and stimulation parameters are transmitted back to the pillow topper (FIGURE from provisional).

In another embodiment, the speakers are stereo and alternate in volume for vestibular stimulation. For purposes of illustration and not limitation, vestibular stimulation can be delivered with a rocking bed that moves the whole body, or through stereo headphones that manipulate the sources of sound more precise, however these methods are unable to also provide an effective basis to deliver all other types of sensory neurostimulation as does the present invention.

The purpose of the present invention is to predict sleep and deliver non-invasive stimulation for enhancement of sleep and waking. Methods of acoustical, vestibular, and olfactory stimulation during sleep have been shown to be effective for enhancing deep sleep. Although photic, haptic, and other non-invasive methods using endogenous mechanisms have yet to be optimized for sleep enhancement, the overall mechanism is hypothesized to be reliable across sensory domains. The present invention takes into account all known methods and yet-to-be validated methods for non-invasive stimulation for enhancing sleep and claims a novel pillow topper implementation with mechanical sensors for delivery thereof, in a manner that is effective within the form constraints whilst being invisible when implemented.

In one embodiment, an array of one accelerometer is at the center of the pillow topper along with a vibrating motor, and two speakers on opposite corners (See FIG. 10). The placement of the speakers in this embodiment is optimal for delivery of acoustical stimulation in a balanced manner, while minimizing the possibility of overstimulation in the scenario where the user is sleeping on her side and her ears are directly over the speakers.

The accelerometer data is processed into magnitude data and extracted into features that are representative of different types and intensities of physiologically significant movements. In one embodiment the processing is done locally in the pillow topper. In another embodiment the processing is transmitted wirelessly via BT to a portable device such as a mobile phone, where the processing occurs remotely and stimulation parameters are transmitted back to the pillow topper as shown in FIG. 1.

In another embodiment, the speakers are stereo and alternate in volume for vestibular stimulation. For purposes of illustration and not limitation, vestibular stimulation can be delivered with a rocking bed that moves the whole body, or through stereo headphones that manipulate the sources of sound more precise, however these methods are unable to also provide an effective basis to deliver all other types of sensory neurostimulation as does the present invention.

The purpose of the present invention is to predict sleep and deliver non-invasive stimulation for enhancement of sleep and waking. Methods of acoustical, vestibular, and olfactory stimulation during sleep have been shown to be effective for enhancing deep sleep. Although photic, haptic, and other non-invasive methods using endogenous mechanisms have yet to be optimized for sleep enhancement, the overall mechanism is hypothesized to be reliable across sensory domains. The present invention takes into account all known methods and yet-to-be validated methods for non-invasive stimulation for enhancing sleep and claims a novel pillow topper implementation with mechanical sensors for delivery thereof, in a manner that is effective within the form constraints whilst being invisible when implemented.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for improving sleep, the system comprising:
   a pillow or pillow topper configured to support a user's head;
   a pillow monitoring portion positioned on or in the pillow or pillow topper; and
   an alarm portion including a buzzer, a radio or a light
   the pillow monitoring portion wired or wirelessly connected to the alarm portion,
   the monitoring portion including a sensor, a processor electronically connected to the sensor, a speaker and a vibrator, and
   the speaker configured to emit acoustic stimulation having a stimulation frequency of less than 1 Hz.

2. The system of claim 1, wherein the sensor is an accelerometer.

3. The system of claim 1, wherein the sensor is configured to detect at least one of body temperature, temperature gradients, blood pressure, heart rate, galvanic skin response, eye movement, or other body movement.

4. The system of claim 1, wherein the processor is configured to process information from the sensor.

5. The system of claim 1, wherein the alarm portion further includes a timer.

6. A method for improving waking, the method comprising:
   providing a monitoring portion on or in a pillow or pillow topper, the monitoring portion including a sensor, a processor electronically connected to the sensor, a speaker configured to emit a beat frequency, and a vibrator;
   determining, via the sensor and the processor, if the sleeping patient is entering a wake-up window, and if so,
   determining, via the processor, if a waking time has been reached, and if so
   activating the speaker to emit a beat frequency tone to improve wakefulness, the beat frequency tone between about 8 Hz and about 12 Hz.

* * * * *